United States Patent [19]

Iso et al.

[11] Patent Number: 4,517,123
[45] Date of Patent: May 14, 1985

[54] CYSTEINE DERIVATIVES OF DISULFIDE FORM

[75] Inventors: Tadashi Iso, Sakai; Masayuki Oya, Ibaraki, both of Japan

[73] Assignee: Santen Pharmaceutical Co., Ltd., Osaka, Japan

[21] Appl. No.: 380,665

[22] PCT Filed: Sep. 18, 1981

[86] PCT No.: PCT/JP81/00235

§ 371 Date: May 4, 1982

§ 102(e) Date: May 4, 1982

[87] PCT Pub. No.: WO82/01000

PCT Pub. Date: Apr. 1, 1982

[30] Foreign Application Priority Data

Sep. 20, 1980 [JP] Japan .................. 55-131349

[51] Int. Cl.$^3$ ............... C07D 210/00; C07C 153/017; C07C 147/02; C07C 101/42
[52] U.S. Cl. .......... 260/239.3 R; 260/455 R; 562/556
[58] Field of Search ........... 260/455 R, 330, 239.3 R; 562/556, 450

[56] References Cited

U.S. PATENT DOCUMENTS 4,241,086 12/1980 Iwao et al. ............ 260/239.3 R
4,255,446 3/1981 Iwao et al. ............ 260/455 R
4,305,958 12/1981 Fujita et al. .......... 260/455 R

FOREIGN PATENT DOCUMENTS 5271928 1/1979 Japan ................ 260/455 R

OTHER PUBLICATIONS

Santen, Chem. Abs., vol. 97, 6782f, p. 657.
Santen Chem. Abstracts, vol. 94, 36350u, p. 375 (1981).

Primary Examiner—Henry R. Jiles
Assistant Examiner—Robert C. Whittenbaugh
Attorney, Agent, or Firm—Frishauf, Holtz, Goodman & Woodward

[57] ABSTRACT

Pharmaceutically active compounds and pharmaceutically acceptable salts thereof having the following formulae

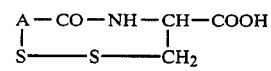

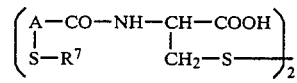

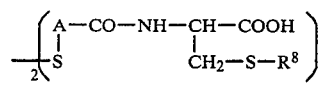

wherein A is a straight or branched chain alkylene group containing 1 to 3 carbon atoms; and $R^7$ and $R^8$ is each a lower alkyl group. These compounds are useful as the active component of pharmacological preparations.

9 Claims, No Drawings

CYSTEINE DERIVATIVES OF DISULFIDE FORM

TECHNICAL FIELD

This invention relates to intra- or intermolecular disulfide compounds represented by the formula

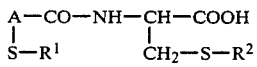

wherein
$R^1$ and $R^2$ each is hydrogen, lower alkyl, aryl, aralkyl, lower alkanoyl or aroyl;
A is straight or branched alkylene containing 1 to 3 carbon atoms.

BACKGROUND OF THE TECHNICAL FIELD

Cysteine derivatives, represented by the formula [I] wherein $R^1$ and $R^2$ are hydrogen or acyl group, are known as useful agents for the treatment of liver damage, rheumatic diseases and cataracts (for example, Japanese Kokai Tokkyo Koho No. Sho 53-5112, 54-5916, 55-51020, 55-51021, 55-51054 and 55-92315 ).

But disulfide derivatives of the oxidized form of the compound, represented by the formula [I] wherein at least one of $R^1$ and $R^2$ is hydrogen, are not disclosed.

DETAILED DESCRIPTION OF THIS INVENTION

The compounds of this invention are novel compounds and we found that they show a suppresive effect toward liver damage and cataracts and have an antirheumatic effect.

The compounds of this invention are more stable than the known compounds mentioned above, so they have advantages for manufacturing and pharmaceutical preparation.

The compounds of this invention are synthesized by the following methods, exemplified by (a) and (b).

(a) The compounds of this invention are synthesized by oxidation (oxidizing agent is metal salts, oxygen, halogen, hydrogenperoxide, etc.) of the compounds represented by the formula [II],

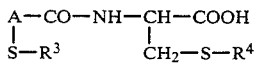

wherein
$R^3$ and $R^4$ each is lower alkyl, aryl, aralkyl, loweralkanoyl or aroyl, but at least one of them is hydrogen.

(b) The compounds of this invention are synthesized by the reaction of the active derivative (for example, acid halide, mixed anhydride or active ester) of the compounds of the formula [III],

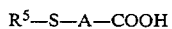

wherein
$R^5$ is hydrogen, lower alkyl, aryl, aralkyl, loweralkanoyl, aroyl or -S-A-COOH,
with the compounds of the formula [IV],

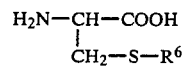

wherein
$R^6$ is hydrogen, lower alkyl, aryl, aralkyl, loweralkanoyl, aroyl or,

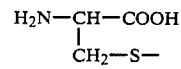

from.

The compound of this invention, synthesized by the above methods, may be converted to the conventional salts such as sodium salt, potassium salt, magnesium salt, calcium salt, aluminium salt, ammonium salt, diethylamine salt, triethanolamine salt, etc. which are acceptable in drug.

The compounds of this invention include the stereoisomers because they have one or more asymmetric carbon atoms.

These stereoisomers are also within the scope of this invention.

Examples are shown below, although this invention is not limited to these Examples.

Best mode of making the invention

EXAMPLE 1

N,N'-Bis[2-methyl-2-(methylthio)propanoyl]-L-cystine

To a stirred solution of 3.1 g (13 mM) of L-cystine in 105 ml of 0.5 N sodium hydroxide, 4.0 g (26 mM) of 2-methyl-2-(methylthio)propanoyl chloride is added dropwise at 5°–10° C. After the addition the reaction mixture is stirred for 45 minutes at the same temperature and for additional 20 minutes at the room temperature. The reaction mixture is washed with ether, acidified with 6N hydrochloric acid and extracted with ethyl acetate. The organic layer is washed with water and dried. Ehtyl acetate is distillated off and the residue is purified by silica gel column chromatography to give 5.1 g (83%) of the titled compound.

mp 128°–129° C. (ethyl acetate-n-hexane)
$[\alpha]_D^{24}$ −157.9° (c=0.9, methanol)
IR(nujol, cm$^{-1}$) 3320, 1730, 1625, 1515 NMR (DMSO-d$_6$, δ) 1.38(12H, s, $(\underline{CH_3})_2$C—), 2.00 (6H, s, $\underline{CH_3}$S—), 3.13(4H, d, J=5.0 Hz, -$\underline{CH_2}$S-), 4.27-4.67(2H, m, $\underline{CH}$COOH), 7.93(2H, d, J=8.0 Hz, —CO$\underline{NH}$—), 12.75(2H, s, COO$\underline{H}$)

Elemental Analysis ($C_{16}H_{28}N_2O_6S_4$) Calcd.: C, 40.65; H, 5.98; N, 5.93; Found: C, 40.88; H, 5.98; N, 5.69.

EXAMPLE 2

N,N'-[2,2'-Dithiobis(2-methylpropanoyl)]bis(S-methyl-L-cysteine) By substituting 5.0 g(37 mM) of S-methyl-L/cysteine and 2.9 g (19 mM) of 2,2'-dithiobis (2-methylpropanoyl)dichloride in the procedure of Example 1, 7.0 g (80%) of the titled compound is obtained.

mp 81°–85° C. (chloroform)
$[\alpha]_D^{24}$ +4.3° (c=1.0, methanol)
IR (nujol, cm$^{-1}$)3310, 1725, 1610 NMR (DMSO-d$_6$, δ) 1.43(12H, s, $(\underline{CH_3})_2$C-), 2.05(6H, s, -CH$_2$S$\underline{CH_3}$), 2.87(4H, d, J=6.0 Hz, -$\underline{CH_2}$S-), 4.17-4.53(2H, m, -$\underline{CH}$COOH), 7.83(2H, d, J=8.0 Hz, —CO$\underline{NH}$—), 8.20(2H, s, COO$\underline{H}$)

Elemental Analysis ($C_{16}H_{28}N_2O_6S_4$) Calcd.: C, 40.65; H, 5.98; N, 5.93; Found: C, 40.20; H, 5.71; N, 5.69.

EXAMPLE 3

(4R)-7,7-Dimethyl-6-oxo-3,4,6,7-tetrahydro-1,2,5-dithiazepine-4-carboxylic acid, also named tetrahydro-7,7-dimethyl-6-oxo-3H-1,2,5-dithiazepine-4-carboxylic acid 1.0 g (4.5 mM) of N-(2-mercapto-2-methylpropanoyl)-L-cysteine and 0.25 g (1.0 mM) of copper sulfate pentahydrate are dissolved in 0.01 M phosphate buffer (pH 7.0). The solution is stirred for 24 hours while bubbling with air. The reaction mixture is acidified with hydrochloric acid and extracted with ethyl acetate The organic layer is washed with saturated sodium chloride solution and dried over magnesium sulfate. Ethyl acetate is distillated off and purified by silica gel column chromatography to give 0.45 g (45%) of the titled compound.

mp 173°–175° C. (ether)

IR (KBr, cm$^{-1}$) 3260, 1750, 1708, 1615

NMR (CDCl$_3$, δ) 1.53(3H, s, $\underline{CH_3}$-), 1.66(3H, s, $\underline{CH_3}$-), 2.65(1H, dd, J=12.0, 12.0 Hz, C$_3$-H$_A$), 3.38(1H, dd, J=4.0, 12.0 Hz, C$_3$-H$_B$), 5.31(1H,ddd, J=4.0, 8.0, 12.0 Hz, C$_4$-H), 8.43(1H, d, J=8.0 Hz, $\underline{NH}$-), 13.0(1H, s, COO$\underline{H}$) CIMS (i-C$_4$H$_{10}$) m/z; 222 ($\overline{MH^+}$)

Utility in an industrial field

The compounds of this invention are useful agents for the treatment of liver damage, rheumatic disease, and cataracts, and they are more stable than the known cysteine derivatives, so they have advantages for manufacturing and pharmaceutical preparation.

What we claim is

1. A compound of the formula

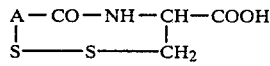

wherein

A is a straight or branched alkylene group containing 1 to 3 carbon atoms, and pharmaceutically acceptable salts thereof.

2. A compound of the formula

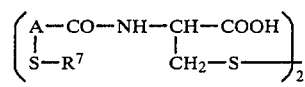

wherein

A is a straight or branched alkylene group containing 1 to 3 carbon atoms; and

R$^7$ is a lower alkyl group, and pharmaceutically acceptable salts thereof.

3. A compound of the formula

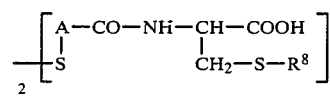

wherein

A is a straight or branched alkylene group containing 1 to 3 carbon atoms; and

R$^8$ is a lower alkyl group, and pharmaceutically salts thereof.

4. Tetrahydro-7,7-dimethyl-6-oxo-3H-1,2,5-dithiazepine-4-carboxylic acid of the formula of claim 1.

5. N,N′-Bis(2-methyl-2-(methylthio)propanoyl)-L-cystine of the formula of claim 2.

6. N,N′-(2,2′-Dithiobis(2-methylpropanoyl))bis(S-methyl-L-cysteine) of the formula of claim 3.

7. The compound of claim 1 wherein said pharmaceutically acceptable salts are selected from the group consisting of sodium salts, potassium salts, magnesium salts, calcium salts, aluminum salts, ammonium salts, diethylamine salts, and triethanolamine salts.

8. The compound of claim 2 wherein said pharmaceutically acceptable salts are selected from the group consisting of sodium salts, potassium salts, magnesium salts, calcium salts, aluminium salts, ammonium salts, diethylamine salts, and triethanolamine salts.

9. The compound of claim 3 wherein said pharmaceutically acceptable salts are selected from the group consisting of sodium salts, potassium salts, magnesium salts, calcium salts, aluminium salts, ammonium salts, diethylamine salts, and triethanolamine salts.

* * * * *